United States Patent [19]

Berg

[11] 4,299,668
[45] Nov. 10, 1981

[54] SEPARATION OF ETHYLBENZENE FROM PARA- AND META-XYLENES BY EXTRACTIVE DISTILLATION

[75] Inventor: Lloyd Berg, Bozeman, Mont.

[73] Assignee: International Synthetic Rubber Co., Ltd., London, England

[21] Appl. No.: 236,998

[22] Filed: Feb. 23, 1981

[51] Int. Cl.³ .......................... B01D 3/40; C07C 7/00
[52] U.S. Cl. ........................................ 203/51; 203/56; 203/63; 203/65; 203/67; 585/805; 585/864
[58] Field of Search .................. 203/51, 56, 63, 65, 203/67; 585/805, 864

[56] References Cited

U.S. PATENT DOCUMENTS

| 2,532,031 | 11/1950 | Nixon et al. | 203/50 |
| 2,567,228 | 9/1951 | Morrell et al. | 585/805 |
| 2,721,170 | 10/1955 | Johnson | 585/805 |
| 2,799,629 | 7/1957 | Clough et al. | 203/51 |
| 3,105,017 | 9/1963 | Amir et al. | 203/67 |
| 3,356,593 | 12/1967 | Suzuki et al. | 203/51 |

Primary Examiner—Wilbur L. Bascomb, Jr.

[57] ABSTRACT

Ethylbenzene and para-xylene and/or meta-xylene are difficult to separate by distillation because they boil only 2.3 C.° and 3.1 C.° apart. Ethylbenzene can be readily separated from the xylenes by using extractive distillation in which the extractive distillation agent is a mixture of pentachlorophenol admixed with certain chlorinated and/or oxygenated organic compounds boiling higher than the xylenes. A typical mixture comprises pentachlorophenol, benzene hexachloride and 1,2,4-trichlorobenzene.

12 Claims, No Drawings

SEPARATION OF ETHYLBENZENE FROM PARA- AND META-XYLENES BY EXTRACTIVE DISTILLATION

FIELD OF THE INVENTION

This invention relates to a method for separating ethylbenzene from the xylenes using mixtures of two or more compounds as extractive agents in extractive distillation.

DESCRIPTION OF THE PRIOR ART

Extractive distillation is the method of separating close boiling compounds by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. The extractive agent should boil higher than any of the close boiling liquids being separated and not form minimum boiling azeotropes with them. Usually the extractive agent is introduced a few plates from the top of the column to insure that none of the extractive agent is carried over with the lowest boiling component. This usually requires that the extractive agent boil twenty Centigrade degrees or more higher than the lowest boiling component.

At the bottom of a continuous column, the less volatile components of the close boiling mixtures and the extractive agent are continuously removed from the column. The usual methods of separation of these two components are the use of another rectification column, cooling and phase separation, or solvent extraction.

The separation of ethylbenzene from p-xylene and/or m-xylene by extractive distillation has been reported. Amir, U.S. Pat. No. 3,105,017 described the use of single compounds to effect this separation and he prefers 1,2,4-trichlorobenzene. This compound increases the relative volatility from 1.06 to 1.116. Nixon, U.S. Pat. Nos. 2,532,031 and 2,638,441 reported that antimony trichloride gave a relative volatility of 1.15. Anstey, British Pat. Nos. 1,257,024-5 used phosphazines to effect this separation.

The advantage of using extractive distillation in this separation can be seen in Table I below. To separate ethylbenzene from p-xylene in 99% purity by conventional rectification requires a minimum of 157 theoretical plates at total reflux ratio. With an extractive distillation agent such as 1,2,4-trichlorobenzene, the relative volatility goes to 1.11 and only 87 plates are now required. The best extractive distillation agents that I have discovered push the relative volatility up to about 1.25 and Table I shows that they will reduce the plate requirement to 41 plates.

TABLE I

Theoretical Plates Required vs. Relative Volatility for Ethylbenzene - p-Xylene Separation.

| Relative Volatility | Theor. Plates Req'd. at Total Reflux |
| --- | --- |
| 1.06 | 157 |
| 1.08 | 118 |
| 1.10 | 97 |
| 1.11 | 87 |
| 1.13 | 75 |
| 1.15 | 66 |
| 1.17 | 58 |
| 1.20 | 50 |
| 1.23 | 45 |
| 1.25 | 41 |
| 1.27 | 38 |

Extractive distillation typically requires the addition of an equal amount to twice as much extractive agent as close boiling compounds on each plate in the rectification column. The extractive distillation agent should be heated to about the same temperature as the plate into which it is introduced. Thus extractive distillation imposes an additional heat requirement on the column as well as somewhat larger plates for the same product output. To be economically attractive, the extractive distillation system must save more in the reduction of the number of theoretical plates and the size of the column than it adds in the cost of larger plates and additional heat requirement. This will vary depending on the difficulty of the separation and the cost of heat. I found that in the separation of ethylbenzene from p-xylene and/or m-xylene, the extractive agent should increase the relative volatility to about 1.2 to make the process economically attractive under the equipment and heat costs in effect at the time of my investigation.

Another consideration in the selection of the extractive distillation agent is its recovery from the bottoms product. The usual method is by rectification in another column. In order to keep the cost of this operation to a minimum, an appreciable boiling point difference between the the compound being separated and the extractive agent is desirable. I recommend twenty Centigrade degrees or more difference.

Ethylbenzene is the major precursor to most processes for producing styrene. Styrene is used principally in plastics manufacture. In the preparation of high polymers, extreme purity is absolutely necessary. It is the presence of impurities that stops chain growth and prevents polymerization to the desired molecular weight. To make high purity styrene, it is necessary to use high purity ethylbenzene. Ethylbenzene is frequently found admixed with its isomers, the xylenes. Since ethylbenzene boils 2.3 Centigrade degrees from p-xylene and 3.1 Centigrade degrees from m-xylene, the separation of ethylbenzene from these xylenes by conventional rectification to produce high purity ethylbenzene is almost impossible. One of the major sources of ethylbenzene is the $C_8$ fraction of hydroformed naphthenic petroleum and here the xylenes will be present with the ethylbenzene.

OBJECTIVE OF THE INVENTION

The object of this invention is to provide a process or method of extractive distillation that will enhance the apparent relative volatility of ethylbenzene and the xylenes in their separation in a rectification column. It is a particular object of this invention to identify suitable mixtures of chlorinated organic compounds which will increase the apparent relative volatility of ethylbenzene to p-xylene and/or m-xylene to about 1.2. It is a further object of this invention to identify chlorinated organic compounds which, in addition to the above constraints, are stable, can be separated from the xylenes by rectification with relatively few theoretical plates and can be recycled to the extractive distillation column and reused with little decomposition.

SUMMARY OF THE INVENTION

The objects of this invention are provided by a process for separating ethylbenzene from p-xylene and/or m-xylene using a mixture of pentachlorophenol admixed with certain chlorinated and/or oxygenated organic compounds as the agent in extractive distillation.

DETAILED ELABORATION OF THE INVENTION

I have discovered that a mixture of pentachlorophenol with one or more solvents when used as the agent in extractive distillation to separate ethylbenzene from p-xylene and/or m-xylene, will give a relative volatility of 1.18 to 1.28 when the amount of agent is between one and two parts per part of ethylbenzene—xylene mixture.

U.S. Pat. No. 3,105,017 indicates that improved yield and purity of ethylbenzene may be obtained from mixtures thereof with xylenes by distilling the mixture in the presence of extractive solvents including various polychlorinated benzenes. While it is stated that "Mixtures of two or more of the compounds of the present invention may be used as the extractive distillation solvent", no examples of such mixtures are cited whereas in actual practice it has been found that unless the particular polychlorinated benzenes are carefully and correctly selected and combined, the relative volatility of such a mixture may be no higher, and sometimes is lower than that of the individual polychlorinated benzenes when used alone. Thus, for example, the value of relative volatility for o-dichlorobenzene used in distilling a mixture containing equal parts of ethylbenzene - p-xylene is 1.10. When p-dichlorobenzene is used to effect this separation, the relative volatility is 1.11. On the other hand, when the extractive solvent contains equal parts of ortho and paradichlorobenzenes and the ratio of these compounds used in in distilling a mixture of ethylbenzene and p-xylene is 1:1:1:1, the value of the relative volatility is only 1.05. When the mixture being distilled contains ethylbenzene, p-xylene, o-dichlorobenzene and p-dichlorobenzene in the ratio of 1:1:1/2:1/2, the value of the relative volatility is 1.08 and a mixture containing ethylbenzene and p-xylene together with a mixture of ortho and para-dichlorobenzenes in the ratio of 1:1:1/3:1/3 is found to have a relative volatility of 1.08.

The value of relative volatility for mixtures of polychlorinated benzenes used as extractive distillation agents also varies with the ratio of the agent to the hydrocarbon and with the ratio of the ethylbenzene to the xylene in the hydrocarbon mixture being distilled. It also varies considerably with variations in temperature and at different points in the fractionating column. Despite these facts, it has been found that relative volatility values exceeding those of the individual constituents are consistently obtained provided the extractive solvent is a mixture of pentachlorophenol in one or more additional solvents which are polychlorophenols, polychlorinated benzenes, trichloropropane and/or glycol ethers. Such mixtures are found to possess unexpectedly high relative volatilities, they maintain their value throughout the changing ethylbenzene—xylene concentration range in the rectifying column and the ratio of the extractive agents to the material being distilled is relatively moderate.

Table II shows the relative volatility of ethylbenzene and p-xylene or m-xylene with a number of solvents which when used singly give only moderate to no increase in relative volatility but which when properly combined in mixtures of two or more, greatly enhance the relative volatility

TABLE II

Relative Volatility of Several Pure Compounds with Ethylbenzene and p- and/or m-Xylene.

| Extractive Agent | Ratio: Hydrocarbon to Extractive Agent | Relative Volatility EtBn-p-X | Relative Volatility EtBn-m-X |
|---|---|---|---|
| Pentachlorophenol | — | solid, melts too high | |
| Polychlorobenzene | 1:1 | 1.16 | |
|  | 2:3 | 1.14 | |
| 1,2,4-Trichlorobenzene | 1:1 | 1.11 | 1.08 |
|  | 2:1 | 1.11 | 1.09 |
| 1,2,3-Trichloropropane | 1:1 | 1.11 | |
|  | 1:2 | 1.10 | |
| 2,4-Dichlorotoluene | 1:1 | 1.06 | |
|  | 1:2 | 1.06 | |
| Benzene hexachloride | 1:1 | 1.07 | |
|  | 2:1 | 1.13 | |
| 2,3,4,6-Tetrachlorophenol | 1:1 | 1.20 | 1.16 |
|  | 2:1 | 1.12 | 1.17 |
| n-Butoxyethanol | 2:1 | 1.04 | |
| 1,2,4,5-Tetrachlorobenzene | — | solid, melts too high | |

Table III shows the relative volatility of ethylbenzene and p-xylene or m-xylene with pentachlorophenol combined with one additional compound. Of the binarys listed, only one, pentachlorophenol and 2,3,4,6-tetrachlorophenol are attractive. One combination shown, pentachlorophenol and 1,2,3-trichloropropane, is poorer than no extractive agent at all.

TABLE III

Relative Volatilities of Several Two-Component Mixtures with Ethylbenzene and p-Xylene or m-Xylene.

| Extractive Agent | Ratio: Hydrocarbon to Extractive Agent | Relative Volatility EtBn-p-X | Relative Volatility EtBn-m-X |
|---|---|---|---|
| 50% Pentachlorophenol 50% Polychlorobenzene | 2:1 | 1.12 | |
| 50% Pentachlorophenol 50% 1,2,4-Trichlorobenzene | 1:1 | 1.14 | |
| 50% Pentachlorophenol 50% 1,2,4-Trichlorobenzene | 2:1 | 1.09 | |
|  | 1:1 | 1.16 | |
| 75% Pentachlorophenol 25% 1,2,3-Trichloropropane | 2:1 | 1.04 | |
|  | 1:1 | 1.03 | |
| 25% Pentachlorophenol 75% 2,4-Dichlorotoluene | 2:1 | 1.10 | |
|  | 1:1 | 1.14 | |
| 85% Pentachlorophenol 15% Benzene hexachloride | 2:1 | 1.18 | |
|  | 1:1 | 1.08 | |
| 50% Pentachlorophenol 50% 2,3,4,6-Tetrachlorophenol | 2:3 | 1.23 | 1.27 |
|  | 1:2 | 1.25 | 1.21 |
| 50% Pentachlorophenol 50% n-Butoxyethanol | 2:1 | 1.09 | |
|  | 1:1 | 1.14 | |
| 50% Pentachlorophenol 50% 1,2,4,5-Tetrachlorobenzene | 2:1 | 1.10 | |
|  | 1:1 | 1.13 | |

None of these compounds by themselves or when combined in most of the binarys are particularly attractive in regards to their separation capability. However when these compounds are combined in the following way, as shown in Table IV, the performance of the combination far exceeds that of the individual components

TABLE IV

Relative Volatility With Multicomponent Extractive Agents.

| Extractive Agent | Ratio: Hydrocarbon to Extractive Agent | Relative Volatility Ethylbenzene - p-Xylene |
|---|---|---|
| 38% Pentachlorophenol<br>24% 2,3,4,6-Tetrachlorophenol<br>38% 1,2,4-Trichlorobenzene | 2:1 | 1.243 |
| 38% Pentachlorophenol<br>24% 2,3,4,6-Tetrachlorophenol<br>38% 2,4-Dichlorotoluene | 2:1 | 1.231 |
| 34% Pentachlorophenol<br>33% Benzene hexachloride<br>33% 2,4-Dichlorotoluene | 2:1 | 1.253 |
| 25% Pentachlorophenol<br>25% Polychlorobenzenes<br>25% 1,2,4,5-Tetrachlorobenzene<br>25% n-Butoxyethanol | 2:1 | 1.192 |
| 27% Pentachlorophenol<br>27% Polychlorobenzenes<br>26% 1,2,4,5-Tetrachlorobenzene<br>20% 2,4-Dichlorotoluene | 2:1 | 1.178 |
| 25% Pentachlorophenol<br>25% Polychlorobenzenes<br>25% Benzene Hexachloride<br>25% 1,2,4-Trichlorobenzene | 2:1 | 1.266 |
| 34% Pentachlorophenol<br>33% Polychlorobenzenes<br>33% 1,2,4-Trichlorobenzene | 2:1 | 1.202 |
| 26% Pentachlorophenol<br>52% Polychlorobenzenes<br>22% 1,2,3-Trichloropropane | 2:1 | 1.180 |
| 34% Pentachlorophenol<br>33% Benzene hexachloride<br>33% 1,2,4-Trichlorobenzene | 2:1 | 1.276 |
| 50% Pentachlorophenol<br>25% Benzene hexachloride<br>25% Polychlorobenzenes | 2:1 | 1.218 |

Table IV—Relative Volatility With Multicomponent Extractive Agents.

The data presented in Tables II and III were obtained in a glass vapor-liquid equilibrium still of the Othmer design. That in Table IV were obtained from either a one-inch diameter glass perforated plate Oldershaw column or a two-inch diameter perforated plate glass rectifying column.

THE USEFULNESS OF THE INVENTION

The usefulness or utility of this invention can be demonstrated by referring to the data presented in Tables I and IV. When ethylbenzene is separated from p-xylene by rectification in 99% purity, 157 theoretical plates are required at total reflux, somewhat more under a finite reflux ratio. Table IV shows that a mixture of pentachlorophenol, benzene hexachloride and 2,4-dichlorotoluene change the relative volatility to 1.253. From Table I it is apparent that now only 41 theoretical plates will be required to effect the separation of ethylbenzene from p-xylene in 99% purity.

WORKING EXAMPLES

Example 1

A mixture comprising 50 grams of ethylbenzene and 50 grams of p-xylene was charged to an Othmer vapor-liquid equilibrium still and refluxed for six hours. Samples of the vapor and liquid were removed and analysed by gas chromatography. The vapor contained 51.0% ethylbenzene and 49p-xylene, the liquid 49.5% ethylbenzene and 50.5% ethylbenzene and 49% p-xylene, the liquid 49.5% ethylbenzene and 50.5% p-xylene. This indicates a relative volatility of ethylbenzene to p-xylene of 1.06. This has been confirmed by numerous other investigators.

Example 2

A mixture comprising 50 grams of ethylbenzene and 50 grams of m-xylene was charged to the Othmer vapor-liquid equilibrium still and refluxed for six hours. Samples of the vapor and liquid were removed and analysed. The vapor contained 51.2% ethylbenzene and 48.8% m-xylene, the liquid 49.3% ethylbenzene and 50.7% m-xylene. This indicates a relative volatility of ethylbenzene to m-xylene of 1.08. This too is the value reported in the literature.

Example 3

A mixture comprising 25 grams ethylbenzene, 25 grams p-xylene, 17 grams pentachlorophenol, 17 grams benzene hexachloride and 17 grams 1,2,4-trichlorobenzene was charged to the vapor-liquid equilibrium still and refluxed for thirteen hours. Analyses indicated a vapor composition of 52.5% ethylbenzene 47.5% p-xylene and a liquid composition of 47.5% ethylbenzene 52.5% p-xylene. This indicates a relative volatility of 1.22.

Example 4

A mixture comprising 20 grams ethylbenzene, 20 grams p-xylene, 20 grams pentachlorophenol, 20 grams benzene hexachloride and 20 grams 1,2,4-trichlorobenzene was charged to the vapor-liquid equilibrium still and refluxed for eleven hours. Analyses indicated a vapor composition of 51.6% ethylbenzene 48.4% p-xylene and a liquid composition of 45.8% ethylbenzene 54.2% p-xylene. This indicates a relative volatility of 1.26.

Example 5

A mixture comprising 20 grams ethylbenzene, 20 grams m-xylene, 20 grams pentachlorophenol, 20 grams benzene hexachloride and 20 grams 1,2,4-trichlorobenzene was charged to the vapor-liquid equilibrium still and refluxed for twelve hours. Analyses indicated a vapor composition of 52.1% ethylbenzene 47.9% m-xylene and a liquid composition of 45.3% ethylbenzene 54.7% m-xylene. This indicates a relative volatility of 1.32.

Example 6

A column consisting of two twenty-plate sections of one-inch diameter glass perforated plates equipped with a vacuum jacket was employed. The column was fitted with a Corad constant reflux ratio distilling head. Between the Corad head and the top of the column, a feed line from a constant flow pump was introduced. The stillpot was equipped with a sampling tube. The column was calibrated with a test mixture of ethylbenzene and p-xylene, which mixture possesses a relative volatility of 1.06. At a constant reflux ratio of 10 to 1, this column calibrated twelve theoretical plates. Then a run was made with a charge of approximately 20% ethylbenzene, 80% p-xylene in the stillpot. The column was operated at total reflux for about an hour and then the pump started at a rate to deliver about one part of extractive agent to one part of ethylbenzene—p-xylene being boiled up. The extractive agent in this example was 33.3% pentachlorophenol, 33.3% benzene hexachloride and 33.4% 1,2,4-trichlorobenzene. The following data were obtained:

| Time, hours | Overhead Composition, % EtBn | Stillpot Composition, % EtBn | Relative Volatility |
|---|---|---|---|
| 1 | 46.67 | 13.64 | 1.153 |
| 2 | 72.15 | 12.16 | 1.276 |
| 3 | 71.03 | 11.95 | 1.273 |

It will be noted that after about two hours, equilibrium has been achieved and the relative volatility remains essentially constant at about 1.27. Without the extractive agent, it would have been 1.06.

Example 7

A column consisting of a forty plate section of two-inch diameter glass perforated plates and equipped with two outer glass tubes, one with a heating element, was employed. A feed tube connected to a constant volume pump was placed above the forty plate section and above that is a three foot section of a packed column. On top of the packed column was a Corad constant reflux ratio distilling head. The stillpot was equipped with a sampling tube. The purpose of the packed section above the pump feed inlet is to fractionate out any of the extractive agent that might have otherwise been carried off with the overhead distillate. The column was calibrated with ethylbenzene—p-xylene and using 1.06 as the relative volatility of this mixture, the forty plate section was found to have fifteen theoretical plates and the packed section 4.5 theoretical plates at 10 : 1 reflux ratio. The pump was started and an extractive agent comprising 50% pentachlorophenol, 25% benzene hexachloride and 25% polychlorobenzenes fed at a rate such that the extractive agent was about equal to the volume of the hydrocarbon boil-up rate. The following data were obtained:

| Time, hours | Overhead Composition, % EtBn | Stillpot Composition, % EtBn | Relative Volatility |
|---|---|---|---|
| 1 | 75.30 | 20.48 | 1.179 |
| 2 | 81.08 | 20.64 | 1.206 |
| 2.5 | 83.14 | 20.47 | 1.218 |

Again it will be noted that it takes about two hours for this equipment to attain equilibrium and that this extractive agent raises the relative volatility from 1.06 to 1.218.

I have shown that the proper combination of one or more compounds with pentachlorophenol will yield separations of ethylbenzene from xylene far better than what is obtainable by any of these compounds individually. The total effect far exceeds the sum of the parts.

The nature of the present invention having been described and illustrated, what I wish to claim as new and useful and secure by Letters Patent is:

1. A method for separating ethylbenzene from p-xylene and/or m-xylene which comprises distilling in a substantially anhydrous condition a mixture of ethylbenzene, p-xylene and/or m-xylene in a rectification column in the presence of an effective amount of an extractive agent comprising pentachlorophenol and one or more other compounds drawn from the group comprising 2,4-dichlorotoluene, 1,2,4-trichlorobenzene, 1,2,4,5-tetrachlorobenzene, polychlorobenzenes (a mixture of tetra- and pentachlorobenzenes), benzene hexachloride, 2,3,4,6-tetrachlorophenol, 1,2,3-trichloropropane, n-butoxyethanol.

2. The method of claim 1 in which the extractive agent is pentachlorophenol, 2,3,4,6-tetrachlorophenol and 1,2,4-trichlorobenzene.

3. The method of claim 1 in which the extractive agent is pentachlorophenol, 2,3,4,6-tetrachlorophenol and 2,4-dichlorotoluene.

4. The method of claim 1 in which the extractive agent is pentachlorophenol, benzene hexachloride and 2,4-dichlorotoluene.

5. The method of claim 1 in which the extractive agent is pentachlorophenol, polychlorobenzenes, 1,2,4,5-tetrachlorobenzene and n-butoxyethanol.

6. The method of claim 1 in which the extractive agent is pentachlorophenol, polychlorobenzenes 1,2,4,5-tetrachlorobenzene and 2,4-dichlorotoluene.

7. The method of claim 1 in which the extractive agent is pentachlorophenol, polychlorobenzenes, benzene hexachloride and 1,2,4-trichlorobenzene.

8. The method of claim 1 in which the extractive agent is pentachlorophenol, polychlorobenzenes and 1,2,4-trichlorobenzene.

9. The method of claim 1 in which the extractive agent is pentachlorophenol, polychlorobenzenes and 1,2,3-trichloropropane.

10. The method of claim 1 in which the extractive agent is pentachlorophenol, benzene hexachloride and 1,2,4-trichlorobenzene.

11. The method of claim 1 in which the extractive agent is pentachlorophenol, polychlorobenzenes and benzene hexachloride.

12. The method of claim 1 in which the extractive agent is pentachlorophenol and 2,3,4,6-tetrachlorophenol.

* * * * *